(12) United States Patent
Patno et al.

(10) Patent No.: US 7,625,746 B2
(45) Date of Patent: Dec. 1, 2009

(54) METHOD OF DENATURING AND FRAGMENTING DNA OR RNA USING ULTRASOUND

(75) Inventors: Tim Patno, Chicago, IL (US); Tom Westberg, Gurnee, IL (US); Michael F. Halblander, Des Plaines, IL (US); Emily R. Beeson, Chicago, IL (US); Benjamin L. Rush, Evanston, IL (US)

(73) Assignee: Nanosphere, Inc., Northbrook, IL (US)

( * ) Notice: Subject to any disclaimer, the term of this patent is extended or adjusted under 35 U.S.C. 154(b) by 0 days.

(21) Appl. No.: 11/491,565

(22) Filed: Jul. 24, 2006

(65) Prior Publication Data

US 2008/0020380 A1    Jan. 24, 2008

(51) Int. Cl.
*C12M 1/00* (2006.01)
(52) U.S. Cl. .................................. 435/283.1
(58) Field of Classification Search ........................ None
See application file for complete search history.

(56) References Cited

U.S. PATENT DOCUMENTS

| | | | | |
|---|---|---|---|---|
| 3,912,455 | A * | 10/1975 | Lichtenstein | 422/61 |
| 6,039,694 | A * | 3/2000 | Larson et al. | 600/459 |
| 6,310,427 | B1 * | 10/2001 | Culbert et al. | 310/337 |
| 6,403,379 | B1 * | 6/2002 | Munson et al. | 436/43 |
| 7,090,974 | B2 * | 8/2006 | Chu | 435/6 |
| 2001/0053525 | A1 | 12/2001 | Chu | |
| 2005/0191620 | A1 * | 9/2005 | McDevitt et al. | 435/5 |

FOREIGN PATENT DOCUMENTS

| | | |
|---|---|---|
| NO | WO 2004/020621 | 3/2004 |
| WO | WO 01/51207 | 7/2001 |
| WO | WO 01/83385 | 11/2001 |
| WO | WO 2004/015089 | 2/2004 |
| WO | WO 2004/020975 | 3/2004 |

OTHER PUBLICATIONS

Li et al. (2003) Tsinghua Sceince and Technology vol. 8, No. 4: pp. 487-492.*
Belgrader et al. (1999) Anal. Chem 71:4232-4236.*

* cited by examiner

*Primary Examiner*—Teresa E Strzelecka
*Assistant Examiner*—Suchira Pande
(74) *Attorney, Agent, or Firm*—Gregory T. Pletta

(57) ABSTRACT

A method and apparatus are provided for processing a DNA or RNA sample within a sample processing module. The method includes the steps of providing a sample well within the sample processing module that contains the DNA or RNA sample, coupling ultrasonic energy from an external source into the sampling well and denaturing and fragmenting the DNA or RNA sample using the ultrasonic energy.

18 Claims, 6 Drawing Sheets

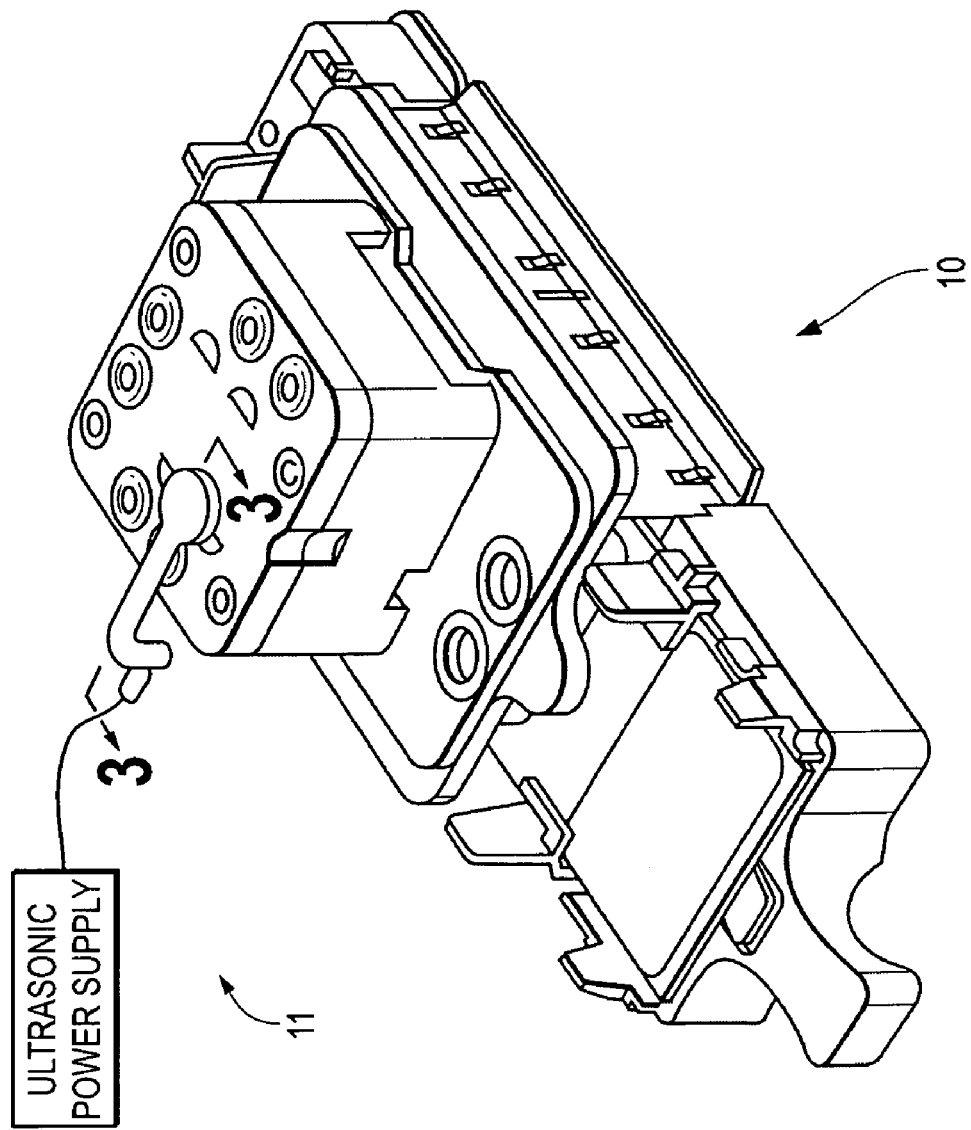

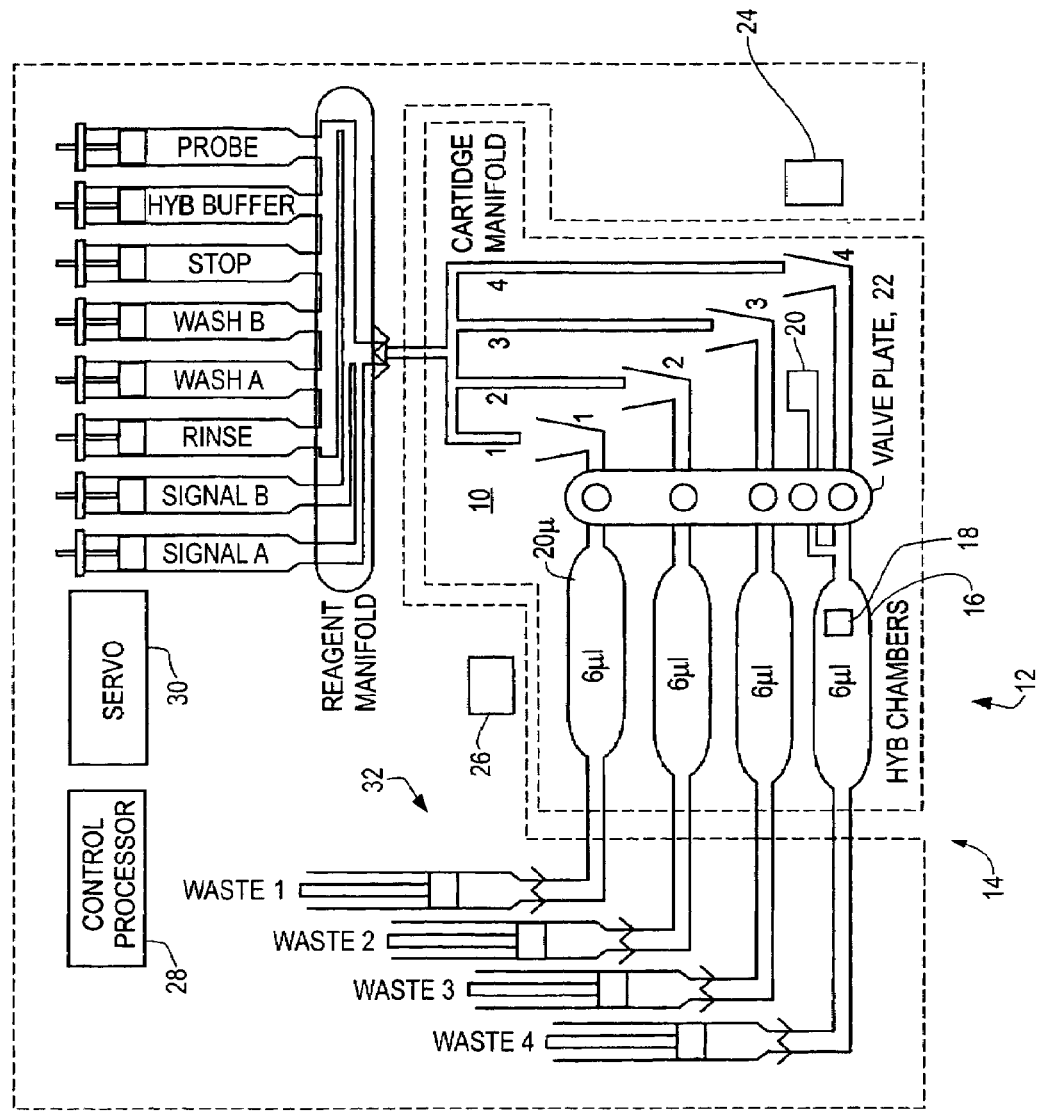

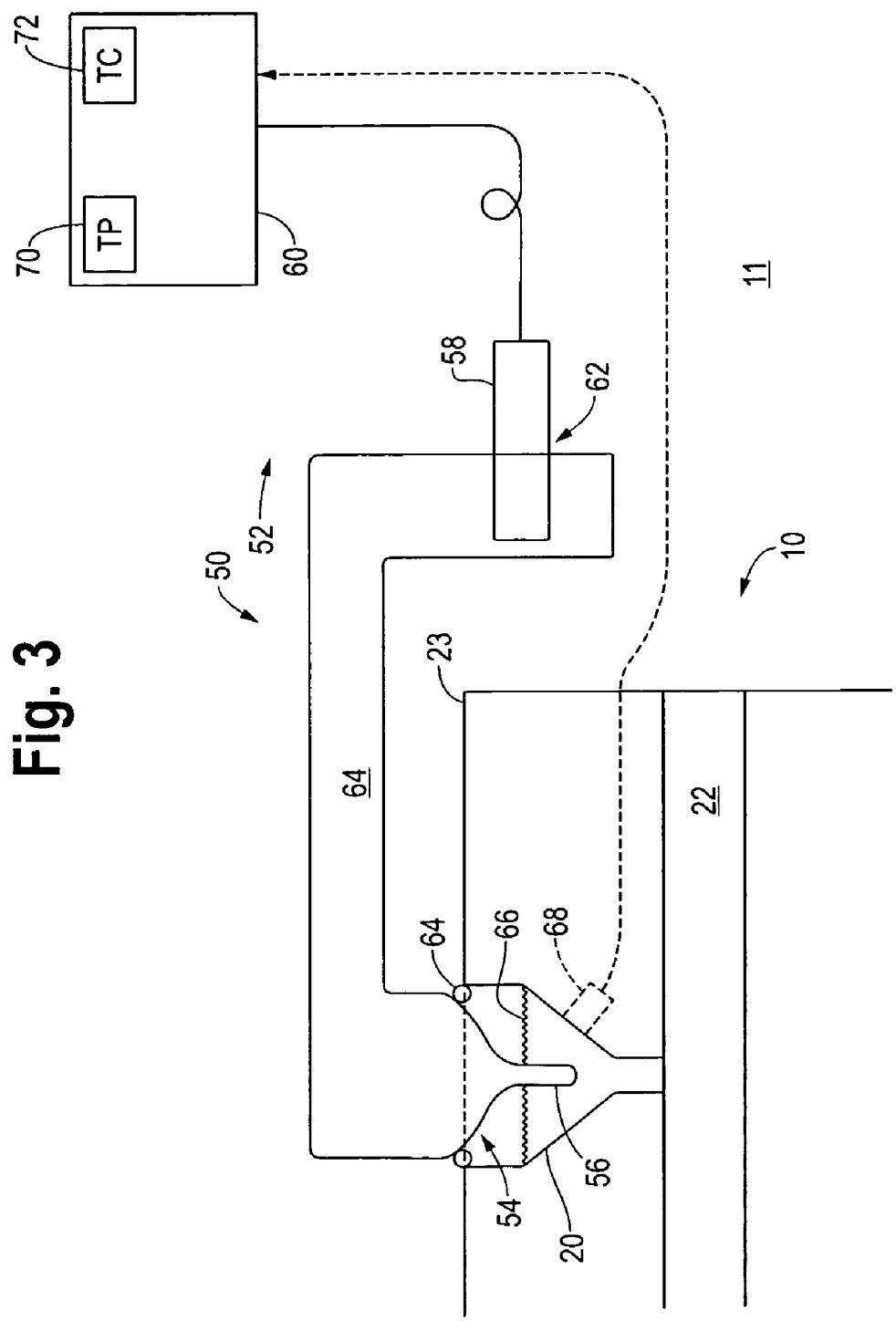

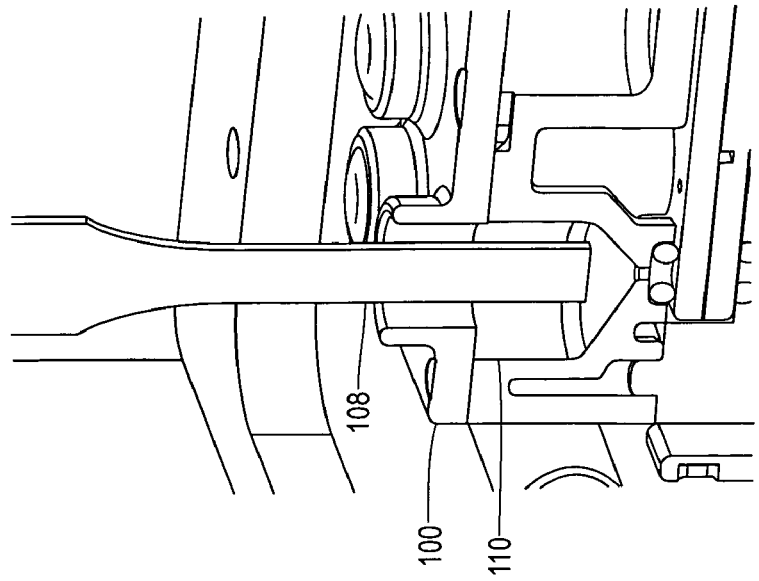
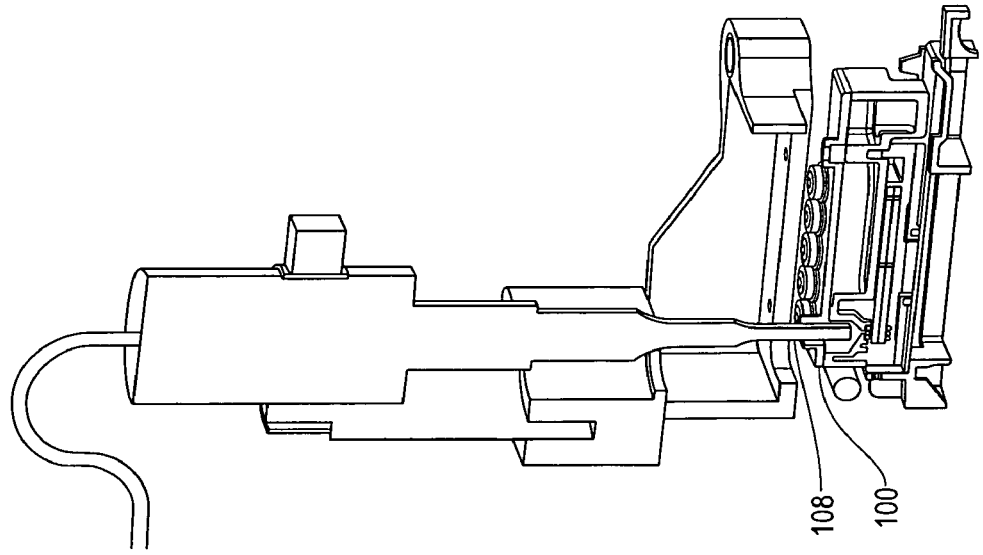
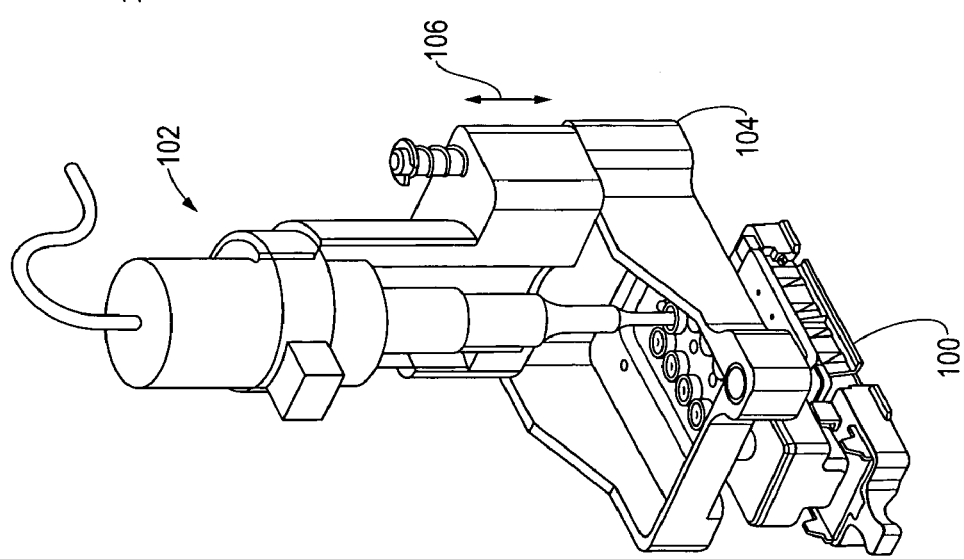

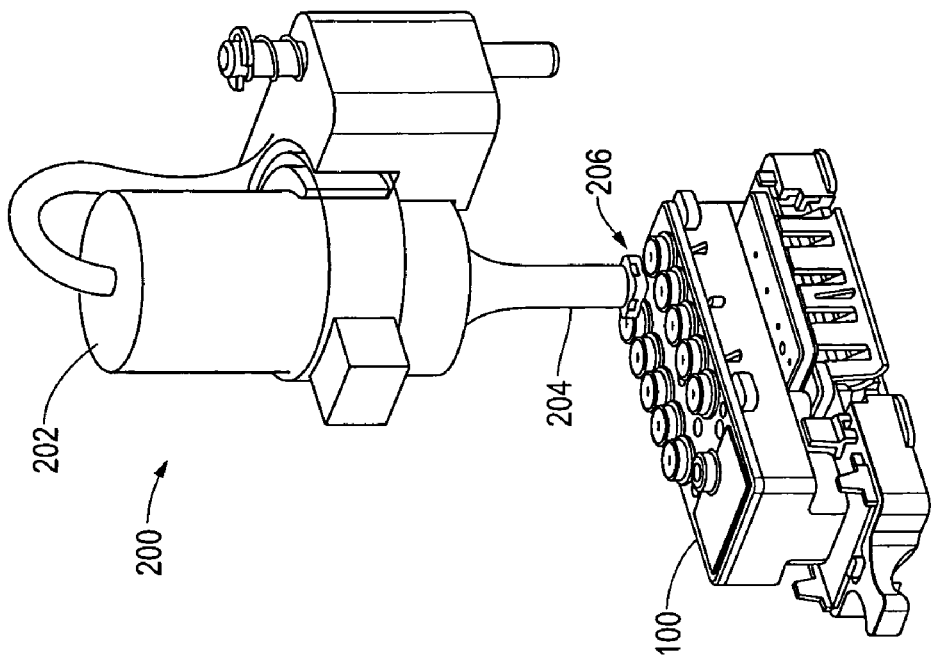
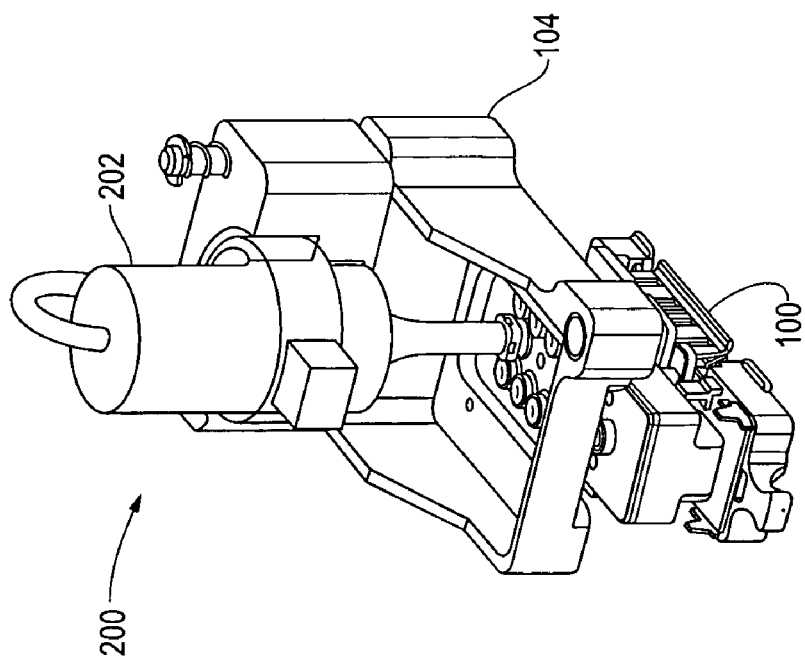

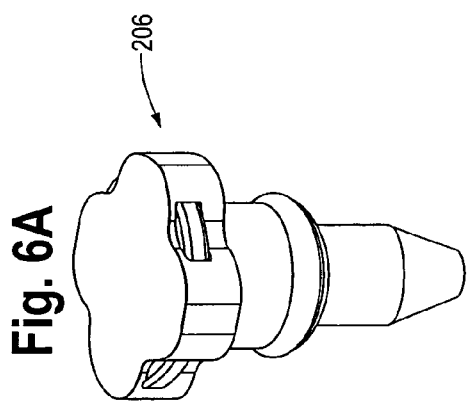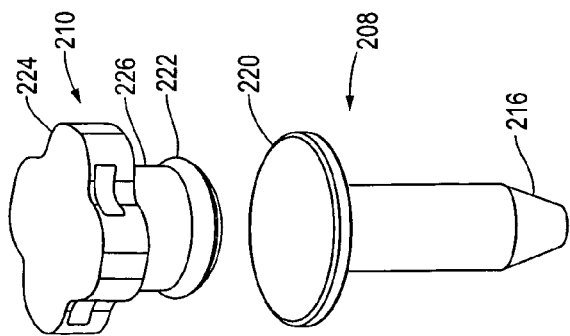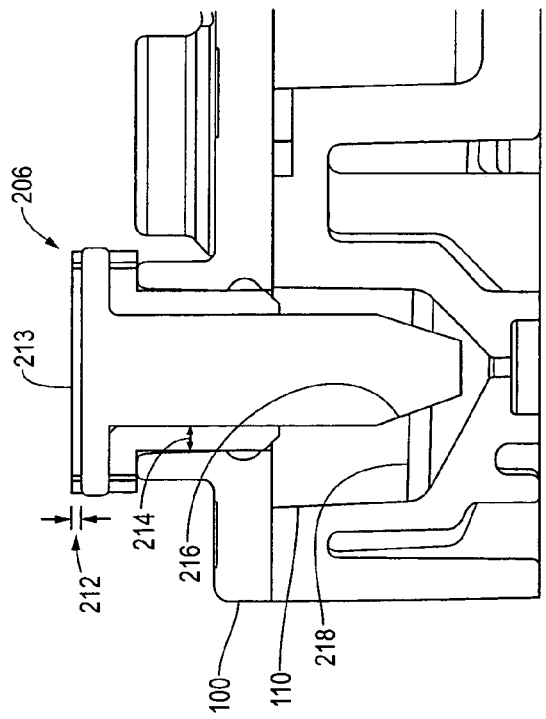

METHOD OF DENATURING AND FRAGMENTING DNA OR RNA USING ULTRASOUND

FIELD OF THE INVENTION

The field of the invention relates to biological testing and more particularly to detecting nucleic acids.

BACKGROUND OF THE INVENTION

Methods of detecting nucleic acids are generally known. In fact, there are a number of methods available for detecting specific nucleic acid sequences.

Known methods include those based upon electrophoresis, polymerase chain reaction (PCR) processes, various hybridization techniques, and a number of other techniques. While these methods are effective, they are all time consuming, costly and subject to significant human error.

For example, one manufacturer makes a microfluidics system that hybridizes a sample to a chip followed by staining of the chip. The hybridization process takes approximately 12 hours. Staining takes approximately 1.5 hours to complete.

Another supplier provides a system that relies upon a single nucleotide polymorphism (SNP) technique. This system uses a microchip for performing multiple assays. Probes are added to a cartridge and the particles move based on charge in an electric field. A detection system may be used for analyzing the cartridges after hybridization with the sample DNA.

Still another supplier provides a device called a Lightcycler that combines PCR amplification and DNA detection into one process. The Lightcycler can use one of two processes for detection. The first process relies upon PCR and hybridization. The second process relies upon PCR and dye and melting curve analysis.

The development of reliable methods for detecting and sequencing nucleic acids is critical to the diagnosis of genetic, bacterial and viral diseases. Because of the importance of health care and disease prevention, a need exists for quicker and cheaper methods of identifying nucleic acids.

SUMMARY

A method and apparatus are provided for processing a DNA or RNA sample within a sample processing module. The method includes the steps of providing a sample well within the sample processing module that contains the DNA or RNA sample, coupling ultrasonic energy from an external source into the sampling well and denaturing and fragmenting the DNA or RNA sample using the ultrasonic energy.

BRIEF DESCRIPTION OF THE DRAWINGS

FIG. 1 is a perspective view of a disposable sample processing module with an ultrasonic device for denaturing and fragmenting DNA or RNA samples within the module under an illustrated embodiment of the invention;

FIG. 2 is a block diagram of the processing system that processes samples placed within the sample processing module;

FIG. 3 is an cut-away side view of the sample processing module of FIG. 1 showing the ultrasonic denaturing device;

FIGS. 4a-c are top perspective, side cut-away and enlarged cut-away views of a disposable sample processing module with an ultrasonic device for denaturing and fragmenting DNA or RNA samples under an alternate embodiment of the invention;

FIGS. 5a-b are top perspective views of a disposable sample processing module with an ultrasonic device for denaturing and fragmenting DNA or RNA samples under another alternate embodiment of the invention;

FIGS. 6a-b depict details of an acoustic coupler and cap used with the ultrasonic device of FIGS. 5a-b; and FIG. 7 is a cut-away view of the acoustic coupler and cap and disposable processing module of FIGS. 5a-b.

DETAILED DESCRIPTION OF AN ILLUSTRATED EMBODIMENT

FIG. 1 depicts a disposable sample processing module 10 that may be used for detecting nucleic acids generally in accordance with an illustrated embodiment of the invention. Shown in conjunction with the module 10 is an ultrasonic denaturing device 11 that functions to denature and fragment DNA or RNA samples placed within the module 10.

FIG. 2 is a simplified block diagram of the nucleic acid detection system 12 in which the module 10 may be used. The system 12 of FIG. 2 may include a processing receptacle 14 that accepts the disposable sample processing module 10. Within the processing unit 12, the sample module 10 may be subjected to a number of processing steps described in more detail below.

The processing system 12 may be used for the detection of any of a number of predetermined target nucleic acids. In fact, any type of nucleic acid may be detected, and the methods may be used for the diagnosis of disease and in sequencing of nucleic acids. Examples of nucleic acids that can be detected by the methods of the invention include genes (e.g., a gene associated with a particular disease), viral RNA and DNA, bacterial DNA, fungal DNA, cDNA, mRNA, RNA and DNA fragments, oligonucleotides, synthetic oligonucleotides, modified oligonucleotides, single-stranded and double-stranded nucleic acids, natural and synthetic nucleic acids, etc. Examples of the uses of the methods of detecting nucleic acids include: the diagnosis and/or monitoring of viral diseases (e.g., human immunodeficiency virus, hepatitis viruses, herpes viruses, cytomegalovirus, and Epstein-Barr virus), bacterial diseases (e.g., tuberculosis, Lyme disease, *H. pylori, Escherichia coli* infections, Legionella infections Mycoplasma infections, Sammonella infections), sexually transmitted diseases (e.g., gonorrhea), inherited disorders (e.g., cystic fibrosis, Duchene muscular dystrophy, phenylketonuria, sickle cell anemia), and cancers (e.g., genes associated with the development of cancer); in forensics; in DNA sequencing; for paternity testing; for cell line authentication; for monitoring gene therapy; and for many other purposes.

In use, a target DNA or RNA sample may be hybridized with an oligonucleotide within one or more of the hybridization chambers 16 located within the processing module 10. Detection of the hybridized materials may be amplified by an autometallographic process where metal ions such as from silver nitrate are reduced to silver atoms that preferentially bind to nanoparticles within an oligonucleotide.

In preparation for testing for a particular nucleic acid, a first oligonucleotide or first group of oligonucleotides with a first predetermined genetic sequence may be disposed on the substrate within one or more of the hybridization zones 16. The first oligonucleotides 18 may have a genetic sequence that is complementary to a first portion of the genetic sequence of the predetermined target nucleic acid.

Probes may be constructed of nanoparticles with one or more strands of second oligonucleotides of a second predetermined genetic sequence attached to the nanoparticles. Nanoparticles useful in the practice of the invention may include metal (e.g., gold, silver, copper, and platinum), semiconductor (e.g., CdSe, CdS, and CdS or CdSe coated with ZnS) and magnetic (e.g., ferromagnetite) colloidal materials. Other nanoparticles useful in the practice of the invention include ZnS, ZnO, $TiO_2$, AgI, AgBr, $HgI_2$, PbS, PbSe, ZnTe, CdTe, $In_2S_3$, $Cd_3P_2$, $Cd_3As_2$, InAs, and GaAs. The size of the nanoparticles is preferably from about 5 nm to about 150 nm (mean diameter), more preferably from about 5 to about 50 nm, most preferably from about 10 to about 30 nm.

The nanoparticles, the second oligonucleotides or both are functionalized in order to attach the oligonucleotides to the nanoparticles. Such methods are known in the art. For instance, oligonucleotides functionalized with alkanethiols at their 3'-termini or 5'-termini readily attach to gold nanoparticles.

The second oligonucleotides may have a sequence that is complementary to a second portion of the genetic sequence of the predetermined target nucleic acid. Preparation of the first and second oligonucleotides and attachment to the respective particles and substrate may be accomplished generally as described in U.S. Pat. No. 6,417,340 assigned to the assignee of the present invention.

In general, the test sample (that may or may not contain the predetermined target nucleic acid) and a hybridization fluid may be mixed in a sample well 20. A probe may be added to the sample well 20 or may be added later. The mixture may be denatured and fragmented before the mixture enters the hybridization chamber. Mixing, denaturing and fragmenting may be accomplished using the ultrasonic device 11.

FIG. 3 shows a cut-away side view of the sample module 10 shown in conjunction with the acoustic denaturing device 11. As shown, the sample module 10 includes an overmolded sample well cover 23 that includes the sample well 20.

The acoustic denaturing device 11 includes an acoustic energy generating system 52 and an acoustic conduit 50 that directly couples acoustic energy into the sample 66. The acoustic energy generating system 52 includes a power supply 60 and transducer 58.

The acoustic conduit 50 may be a tubular structure filled with an acoustic transmission material 64 (e.g., mineral oil) that is designed to receive acoustic energy from a first end and deliver that energy to a second end within the sample processing module 10. The acoustic generating system 52 and conduit 50 has been found to be especially effective in denaturing and fragmenting samples when operated at a frequency above 20 kHz (e.g., approximately 40 kHz).

The transducer 58 and acoustic conduit 50 is designed so that the transducer may enter the conduit 50 and operate in direct contact with the acoustic transmission material 64. An appropriate coupling device 62 (e.g., a septum) may be used to allow the transducer 58 to physically enter the acoustic conduit 50.

The acoustic conduit 50 may include a sample well cap 54 on an end opposite the transducer 58. The sample well cap 54 is an enlarged end of the conduit 50 that functions to close-off and seal the sample well 20. An O-ring 64 may be provided around a lip of the sample well 20 to further aid in the seal between the cap 54 and well 20.

An acoustic horn 56 projects from the sample well cap 54 and extends into the DNA or RNA sample 66. The acoustic horn 56 is a generally converging structure at the end of the acoustic conduit 50 that functions to amplify impinging acoustic energy, thereby increasing a coupling of the acoustic energy into the sample 66. The coupling of the acoustic energy can be characterized as an invasive coupling between an emitter portion of the horn 56 and sample 66 since the horn 56 extends directly into the sample 66.

Control of the ultrasound power supply 60 for denaturing and fragmentation of the sample 66 may occur under any of a number of different formats. Under the first format, an ON-OFF timing sequence may be used to impart energy into the sample. Under a first portion of the sequence, a timing processor 70 within the power supply 60 may subject the sample 66 to a constant stream of ultrasound for a first time period (e.g., one minute) followed by a ON-OFF stream of ultrasound (e.g., 40% ON, 60% OFF) for a second time period (e.g., four minutes).

Under another format, a temperature sensor 68 (e.g., a thermocouple) may be coupled to the sample well 20 as shown in FIG. 3. Under this format, the timing processor 70 within the power supply 60 may subject the sample 66 to a constant stream of ultrasound for a first time period (e.g., one minute) to fragment the DNA or RNA of the sample 66. Following the first time period, a temperature controller 72 may continue to apply ultrasound to the sample 66 while monitoring a temperature of the sample 66. Once the temperature has reached some predetermined denaturization temperature (e.g., 95° C.), the temperature controller 72 may apply ultrasound to the sample 66 as necessary to maintain the predetermined temperature for some time period (e.g., five minutes) to achieve some optimum level of denaturization.

Before addition of the sample 66 to the sample well 20 and denaturing of the sample, it may be assumed that the valve plate 22 is in its closed position to prevent entry of the sample into the hybridization chamber 16. The valve 22 is closed to prevent interaction of the sample with the first oligonucleotide before fragmentation and denaturization are complete.

Once the sample processing module 10 has been prepared by a technician, the module 10 may be inserted into the processing system 12. Upon insertion of the module 10, the ultrasonic denaturing device 11 may be activated to denature the sample. A set of thermoelectric devices 26 may also be disposed against the bottom of the hybridization chamber 16 to heat or cool the hybridization chambers 16. Thermocouples within the processing system 12 may be used to detect and control the temperatures.

The temperature of the contents of the sample well 20 and the hybridization chamber 16 may be carefully controlled to ensure a successful test. The contents of the sample well 20 may be heated to 95° C. for denaturation of the biomolecules (e.g., DNA). Heating of up to 130° C. may be provided for concentration of sample fluids via evaporation. The temperature control may be 95° C.±5° C. and 130° C.±10° C.

Once the temperature of the module 10 has been stabilized, a stepper motor 30 may be activated by a controller 28 to open the valve plate 22. A set of waste pumps 32 may be activated to pull the mixture from the sample well 20 into the hybridization chamber 16. A shuttling motion may be used as described in parent application Ser. No. 10/703,368 to facilitate sample hybridization.

Following hybridization, one or more washing steps may occur with wash solutions. If a probe was not included in the sample, then a probe solution can be added following the first wash and a probe hybridization may occur over a predetermined time period determined by the controller 28. The probe hybridization may be of a duration of 5 to 30 minutes depending upon the application. Another series of washes can be performed following the probe hybridization.

One or more solutions can be added during each processing phase. Typically one solution is added except for during probe hybridization and signal amplification when two solutions may be added in parallel. When two solutions are added, a fluid mixer in the sample module 10 mixes the fluids. The fluid mixer may be the device 11.

Two common fluid fill ports may be used to provide the fluid to the four channels. Each sample well 20, which acts as a repository for the fluids is vented. Once the fluids are added to the sample well, they are pulled through the hybridization chamber 16 via a pump that interfaces uniquely with a single hybridization chamber 16. Cross-contamination of samples is mitigated with the independent flow path design. For a discussion of the use of the sample processing module 10 and its use, the reader is referred to U.S. patent application Ser. No. 10/982,292 filed on Aug. 4, 2005, incorporated herein by reference.

FIGS. 4a-c depicts an acoustic denaturing device (now labeled 102) that may be used with a self-contained sample processing module 100. Self-contained, in this case means that the sample processing module 100 contains the sample and all of the fluids necessary to carry the test to completion. Samples within the module 100 are processed within the processing system 12 in much the same way as with the module 10 except that it is not necessary to provide reagents.

In this case, the acoustic denaturing device 102 is a one-piece, integral device supported by a moveable carriage 104. A servo (not show) raises and lowers 106 the acoustic denaturing device 102. When lowered an acoustic emitter 108 of the device 102 extends into the liquid 66 within a sample well 110 for the direct application of ultrasound. In this regard, FIG. 4a shows a top perspective view of the horn 104 extending into the sample well 110. FIG. 4b is a cut-away view of the module 100 showing the emitter 108 extending into the sample well 100. FIG. 4c is an enlarged view of the sample well 110 and emitter 108. In the case of FIGS. 4a-c, the acoustic denaturing device 102 may operate substantially the same way as the previously described device 11.

FIGS. 5a-b depicts another embodiment of an acoustic denaturing device 200. In the embodiment of FIGS. 5a-b, the acoustic denaturing device 200 is comprised of an acoustic power supply 202 and acoustic conduit.

In the case of FIGS. 5a-b, the application of acoustic energy may be considered to be applied indirectly. Indirectly means that the acoustic conduit includes more than one acoustic transmission element.

In this case, the acoustic conduit may comprise an acoustic transmission coupler (shaft) 204 and a disposable acoustic coupler and cap (acoustic cap) 206 that is inserted into the sample well 110. As with the previous embodiment, the denaturing device 200 may be raised and lowered via a carriage 104.

FIG. 6a shows the acoustic cap 206 alone and FIG. 6b shows an exploded view of the acoustic cap 206. The acoustic cap 206 includes an integrated coupling pin 208 and cap 210. The coupling pin 208 may include a flange 220 on a first end and a horn 216 on a second, opposing end. As above, the horn 216 functions to concentrate acoustic energy in an emitter portion of the pin 208 that enters the liquid 218.

The cap 210 includes an upper portion 224 that encloses the flange 220 and a lower portion 226 that covers and extends down a portion of a shaft of the pin 208. A bottom end of the lower portion 226 contains a groove that extends around a periphery of the lower portion 226 and contains an O-ring 222.

The pin 208 may be fabricated from a material with good acoustic transmission qualities (e.g., aluminum). The cap 206 may be fabricated from a material with moderate acoustic transmission qualities (e.g., hard silicone).

As shown in FIG. 7, a thickness 212 of a top 213 of the cap 210 is relatively small (e.g., 0.5 mm) to ensure good acoustic coupling between the shaft 204 and pin 208. The top 213 is provided to cover the pin 208 and to prevent the pin 208 from being separated from the cap 210.

In contrast, a wall thickness 214 of the lower portion 226 of the cap 210 is made relatively large (e.g., several mm). The relatively large thickness 214 serves the very important function of acoustic isolation that concentrates ultrasonic energy within the sample 218 rather than having the ultrasonic energy leak through the lower portion 226 of the cap 210 into the walls of the chamber 110.

During use, the module 100 is prepared by adding a DNA or RNA sample. Once the DNA or RNA sample has been added to the sample well 110, the entrance to the sample well 110 is sealed with the acoustic cap 206. Sealing the sample well 110 serves the very important function of protecting personnel that handle the module 100 from biological hazards that may be posed by the DNA or RNA sample.

Once the DNA or RNA sample and processing fluids have been added, the module 100 may be inserted into the processing module 12. Once inserted into the processing module 12, the servo may be activated to bring the transmission shaft 204 into contact with the acoustic cap 206. The acoustic source 202 may then be activated to couple acoustic energy into the sample 218 to fragment and denature the sample as discussed above.

In general, the acoustic denaturing devices 11, 102, 200 have been found to denature and fragment the DNA or RNA sample quickly and effectively without the use of chaotropic agents. The ability to denature DNA or RNA samples without chaotropic agents is important because such agents are known to contaminate the DNA or RNA samples.

It is believed that the unusual effectiveness of the ultrasonic devices 11, 102, 200 in denaturing and fragmenting the DNA or RNA samples is related to the unique features of the combination of the processing module and ultrasonic devices 11, 102, 200. For example, the sample well 20, 110 is relatively small with a diameter of only a few millimeters and a cone-shaped bottom and holds a relatively small sample volume of from 20-200 micro liters. In contrast, the emitter 56, 108, 216 may be relatively large by contrast (e.g., 0.5-1.0 mm). The combination of small sample well and large emitter results in a relatively large ratio between the surface area of the emitter versus sample volume. The large ratio and frequency of 40 kHz has been found to be particularly effective.

Tests have shown that the denaturing device 11, 102 is able to denature a DNA or RNA sample is less than 30 seconds. In contrast, the denaturing device 200 has been able to denature DNA or RNA samples in less than 60 seconds with the added safety provided by a closed sample well 110.

A specific embodiment of an ultrasonic denaturing and fragmenting device for use with a disposable sample processing module has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

What is claimed is:

1. An apparatus for processing DNA or RNA samples within a disposable sample processing module comprising:
   a plurality of sample wells within the disposable sample processing module that contains the DNA or RNA samples, the sample wells each defined by opposing sidewall portions and a bottom portion;

a single valve plate that forms the bottom portion of each of the plurality of sample wells, that is movable with respect to the sample wells between first and second positions and where the valve plate blocks a lower end of the samples wells while the valve plate is in the first position;

means for coupling an external source of ultrasonic energy into a sampling well of the plurality of sampling wells; and means extending through an upper end of the sample well into the DNA or RNA sample for denaturing and fragmenting the DNA or RNA sample by applying ultrasonic energy from the ultrasonic source; wherein the valve plate, while in the first position prevents interaction of the DNA or RNA sample with other processing fluids of the disposable processing module before denaturing and fragmenting are complete, and while in the second position allows interaction of the DNA or RNA sample with other processing fluids of the disposable processing module after denaturing and fragmenting are complete.

2. The apparatus for processing a DNA or RNA sample as in claim 1 wherein the means for coupling the external source of ultrasonic energy into the sampling well further comprises an ultrasonic conduit disposed between the source of ultrasonic energy and the sample well.

3. The apparatus for processing the DNA or RNA sample as in claim 2 wherein the ultrasonic conduit further comprises a sample well cap with an ultrasound extension projecting from the sample well cap into the DNA or RNA sample.

4. The apparatus for processing the DNA or RNA sample as in claim 3 wherein the ultrasonic conduit further comprises an ultrasonic transmission fluid.

5. The apparatus for processing the DNA or RNA sample as in claim 4 wherein the ultrasonic transmission fluid further comprises a mineral oil.

6. The apparatus for processing the DNA or RNA sample as in claim 5 further comprising disposing a septum on a distal end of the ultrasonic conduit that accepts an ultrasonic transducer.

7. The apparatus for processing the DNA or RNA sample as in claim 1 further comprising means for measuring a temperature of the DNA or RNA sample.

8. The apparatus for processing the DNA or RNA sample as in claim 7 further comprising means for terminating application of the ultrasonic energy when the DNA or RNA sample reaches a predetermined temperature.

9. An apparatus for processing DNA or RNA samples within a disposable sample processing module comprising:

a plurality of sample wells disposed within the disposable sample processing module that holds the DNA or RNA samples, the sample wells each defined by opposing sidewall portions and a bottom portion;

a single valve plate that forms the bottom portion of each of the sample wells, that is movable with respect to the sample wells between first and second positions and where the valve plate blocks a lower end of the sample chambers while the valve plate is in the first position;

an ultrasonic conduit coupled to a sampling well of the plurality of sampling wells extending through an upper end of the sample well into the DNA or RNA sample; and an ultrasonic source that denatures and fragments the DNA or RNA sample by applying ultrasonic energy to the DNA or RNA sample through the ultrasonic conduit; wherein the valve plate, while in the first position prevents interaction of the DNA or RNA sample with other processing fluids of the disposable processing module before denaturing and fragmenting are complete, and while in the second position allows interaction of the DNA or RNA sample with other processing fluids of the disposable processing module after denaturing and fragmenting are complete.

10. The apparatus for processing the DNA or RNA sample as in claim 9 wherein the ultrasonic conduit further comprises a sample well cap with an ultrasound extension projecting from the sample well cap into the DNA or RNA sample.

11. The apparatus for processing the DNA or RNA sample as in claim 10 wherein the ultrasonic conduit further comprises an ultrasonic transmission fluid.

12. The apparatus for processing the DNA or RNA sample as in claim 11 wherein the ultrasonic transmission fluid further comprises a mineral oil.

13. The apparatus for processing the DNA or RNA sample as in claim 12 further comprising disposing a septum on a distal end of the ultrasonic conduit that accepts an ultrasonic transducer.

14. The apparatus for processing the DNA or RNA sample as in claim 9 further comprising means for measuring a temperature of the DNA or RNA sample.

15. The apparatus for processing the DNA or RNA sample as in claim 14 further comprising means for terminating application of the ultrasonic energy when the DNA or RNA sample reaches a predetermined temperature.

16. The apparatus for processing the DNA or RNA sample as in claim 14 wherein the ultrasonic conduit further comprises an integrated acoustic coupler and cap that seals a top of the sample well and that couples acoustic energy into the DNA or RNA sample within the sample well through the acoustic coupler of the integrated acoustic coupler and cap.

17. The apparatus for processing the DNA or RNA sample as in claim 16 wherein the cap of the acoustic coupler and cap further comprises an acoustic isolator.

18. The apparatus for processing the DNA or RNA sample as in claim 17 wherein the cap of the acoustic coupler and cap further comprises a silicone.

* * * * *